(12) United States Patent
Stine et al.

(10) Patent No.: US 9,963,407 B2
(45) Date of Patent: May 8, 2018

(54) FLUIDIZED CATALYST CIRCULATION REACTOR FOR PARAFFIN OXYDATIVE DEHYDROGENATION

(71) Applicant: UOP LLC, Des Plaines, IL (US)

(72) Inventors: Laurence O. Stine, Western Springs, IL (US); Bipin V. Vora, Naperville, IL (US); Malek Y. S. Ibrahim, Cairo (EG); Daniel H. Wei, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 540 days.

(21) Appl. No.: 13/920,543

(22) Filed: Jun. 18, 2013

(65) Prior Publication Data
US 2014/0371504 A1 Dec. 18, 2014

(51) Int. Cl.
*C07C 5/48* (2006.01)

(52) U.S. Cl.
CPC ............ *C07C 5/48* (2013.01); *C07C 2521/04* (2013.01)

(58) Field of Classification Search
None
See application file for complete search history.

(56) References Cited

U.S. PATENT DOCUMENTS

| | | |
|---|---|---|
| 3,320,331 A | 5/1967 | Gaspar et al. |
| 3,660,520 A | 5/1972 | Hemminger |
| 3,801,672 A | 4/1974 | Bajars |
| 3,856,880 A | 12/1974 | Woskow et al. |
| 4,376,225 A * | 3/1983 | Vora .................. C07C 5/333 585/658 |
| 4,430,517 A | 2/1984 | Imai et al. |
| 4,435,607 A | 3/1984 | Imai et al. |
| 4,599,471 A | 7/1986 | Ward |
| 4,788,371 A | 11/1988 | Imai et al. |
| 4,914,075 A | 4/1990 | Bricker et al. |
| 5,639,929 A | 6/1997 | Bharadwaj et al. |
| 5,656,243 A | 9/1997 | Luckenbach et al. |
| 5,866,737 A | 2/1999 | Hagemeyer et al. |
| 6,072,097 A | 6/2000 | Yokoyama et al. |
| 6,518,476 B1 * | 2/2003 | Culp .................. C07C 2/84 585/655 |
| 6,756,340 B2 | 6/2004 | Voskoboynikov et al. |
| 6,872,364 B2 | 3/2005 | Bierl et al. |
| 7,087,802 B2 | 8/2006 | Schindler et al. |
| 7,223,897 B2 | 5/2007 | Couves et al. |
| 7,674,944 B2 | 3/2010 | Liu |
| 8,202,814 B2 | 6/2012 | Dieterle et al. |

(Continued)

OTHER PUBLICATIONS de Velden et al. "The solids flow in the riser of a Circulating Fluidised Bed (CFB) viewed by Positron Emission Particle Tracking (PPET)", Powder Technology 183 (2008) 290-296.*

(Continued)

*Primary Examiner* — In Suk C Bullock
*Assistant Examiner* — Ali Z Fadhel

(57) ABSTRACT

A process of oxidative dehydrogenation in a fluidized riser reactor is described. Hydrocarbon feed and catalyst are fed to the bottom of the fluidized riser reactor. Part of the hydrogen produced in the dehydrogenation reaction is oxidized using oxygen introduced into the riser reactor through oxygen injection ports to produce the heat required for the dehydrogenation reaction.

20 Claims, 3 Drawing Sheets

(56) References Cited

U.S. PATENT DOCUMENTS

| | | | | |
|---|---|---|---|---|
| 8,519,210 B2* | 8/2013 | Arnold | ............ | C07C 5/48 585/655 |
| 8,846,996 B2* | 9/2014 | Kustov | ............ | B01J 23/002 241/24.12 |
| 2006/0069297 A1 | 3/2006 | Couves et al. | | |
| 2007/0129587 A1* | 6/2007 | Iaccino | ............ | C07C 2/76 585/407 |
| 2008/0161624 A1* | 7/2008 | Glover | ............ | C07C 5/324 585/634 |
| 2009/0292153 A1 | 11/2009 | Cai et al. | | |
| 2010/0094071 A1 | 4/2010 | Olbert et al. | | |
| 2011/0245571 A1 | 10/2011 | Kustov et al. | | |
| 2012/0215045 A1* | 8/2012 | Butler | ............ | C07C 2/84 585/422 |

OTHER PUBLICATIONS

Ahchieva et al., "Oxidative dehydrogenation of ethane in a fluidized . . . ," Applied Catalysis A: General 296 (2005), pp. 176-185.

Rubio et al., "Oxidative Dehydrogenation of Butane in an . . . ," AIChE Journal, vol. 50, No. 7, Jul. 2004, pp. 1510-1522.

Sadykov et al., "Oxidative dehydrogenation of propane over . . . ," Catalysis Today 61 (2000) pp. 93-99.

\* cited by examiner

FLUIDIZED CATALYST CIRCULATION REACTOR FOR PARAFFIN OXYDATIVE DEHYDROGENATION

BACKGROUND OF THE INVENTION

Catalytic dehydrogenation can be used to convert paraffins to the corresponding olefin, e.g., propane to propene, or butane to butene.

FIG. 1 shows one typical arrangement for a moving bed dehydrogenation process 5. The process 5 includes a reactor section 10, a regeneration section 15, and a product recovery section 20.

The reactor section 10 includes one or more reactors 25 (four as shown). The feed 30 is sent to a heat exchanger 35 where it exchanges heat with the reactor effluent 40 to raise the feed temperature. The feed 30 is sent to a preheater 45 where it is heated to the desired inlet temperature. The preheated feed 50 is sent from the preheater 45 to the first reactor 25. Because the dehydrogenation reaction is endothermic, the temperature of the effluent 55 from the first reactor 25 is less than the temperature of the preheated feed 50. The effluent 55 is sent to interstage heaters 60 to raise the temperature to the desired inlet temperature for the next reactor 25.

After the last reactor (in this case the fourth reactor), the effluent 40 is sent to heat exchanger 35, and heat is exchanged with the feed 30. The effluent 40 is then sent to the product recovery section 20.

The catalyst 65 moves through the series of reactors 25. When the catalyst 70 leaves the last reactor 25, it is sent to the regeneration section 15. The regeneration section includes a reactor 75 where the coke on the catalyst is burned off and the catalyst may go through a reconditioning step. The regenerated catalyst 80 is sent back to the first reactor 25.

In the product recovery section 20, the effluent 40 is cooled, compressed, dried, and separated in separator 85. The gas 90 is expanded in expander 95 and then separated into a recycle hydrogen stream 100 and a net separator gas stream 105. The liquid stream 110, which includes the olefin product and unconverted paraffin, is sent for further processing, where the desired olefin product is recovered and the unconverted paraffin is recycled to the dehydrogenation reactor.

FIG. 2 shows a typical arrangement for a cyclic bed dehydrogenation process 115. The process 115 includes a reactor section 120, and a product recovery section similar to that described above (not shown in FIG. 2).

In this process 115, the feed 130 is sent to a heat exchanger 135 where it exchanges heat with the reactor effluent 140 to raise the feed temperature. As shown, there are four reactors 145A-D. Of these, typically one will be operating (145A); one will be purging (145B); one will be regenerating the catalyst, that is, burning of coke and reconditioning if required (145C); and one will be purging and preparing for the next process cycle (145D). The feed 130 is sent to preheaters 150 where it is heated to the desired inlet temperature. The preheated feed 155 is sent from the preheater 150 to the operating reactor 145A.

The effluent 140 from the operating reactor 145A is sent to heat exchanger 135, and heat is exchanged with the feed 130. The effluent 140 is then sent to the product recovery section.

Reactor 145B is being purged. The hydrocarbon feed to the reactor is stopped, and the connection to the effluent is closed. A purge gas 160 is introduced into reactor 145B to remove any hydrocarbon feed from the reactor in preparation for regenerating the catalyst.

Reactor 145C is being regenerated. An oxygen-containing stream 165 is introduced into the reactor so the coke on the catalyst can be burned off, and the catalyst is reconditioned if required.

Reactor 145D is being purged. The oxygen-containing feed to the reactor is stopped. A purge gas 160 is introduced into reactor 145D to remove any residual air/oxygen feed from the reactor in preparation for next processing cycle.

The time duration of steps two, three and four, that is purging, coke burning, and purging is matched with the time duration of the first step, that is the process cycle. In some instances, to match this timing duration, one may use more than one reactor in the processing step.

In paraffin dehydrogenation processes, maximum conversion is limited by equilibrium at the reactor outlet conditions. Feed has to be heated to a high temperature before being fed to a series of adiabatic reactors where dehydrogenation takes place. Depending on the carbon number of the feed being dehydrogenated, this temperature can very from about 450° C. to about 700° C. The lower carbon number feeds, such as ethane, propane, butane ($C_2$-$C_4$), require higher temperatures, in the range of about 600 to about 700° C., compared to those with carbon number, such as decane or dodecane ($C_{10}$, $C_{12}$), which may require temperatures in the range of about 450 to about 550° C. As shown in FIG. 3, at 101 kPa (1 atm) and 550° C., the propylene to propane ratio is 32/68, while at the same temperature, the isobutene to isobutane ratio is 50/50.

The paraffin dehydrogenation reaction is equilibrium limited.

$$C_nH_{2n+2} \rightleftarrows C_nH_{2n}+H_2$$

As shown, the dehydrogenation reaction produces alkenes and hydrogen. Because the reaction is endothermic, the reactor outlet temperature is lower than the inlet temperature. As the temperature declines, so does the equilibrium concentration for alkene, and hence it limits the maximum conversion that can be achieved within each reactor. Furthermore, higher inlet temperature can thermally crack the feed hydrocarbons, resulting in selectivity loss.

Multi-stage heating steps increases the circuit pressure drop and hot residence time much more than the required amount for actual hydrocarbon-catalyst contact, resulting in higher utilities consumption and more undesired thermal reactions. Limited conversion increases the amount of recycled unreacted material, resulting in increases in unit capital costs and operating costs.

There is a need for improved dehydrogenation processes.

SUMMARY OF THE INVENTION

One aspect of the invention involves a process for oxidative dehydrogenating dehydrogenatable hydrocarbons. In one embodiment, the process involves introducing a feed and an oxidative dehydrogenation catalyst into an inlet at a bottom of a fluidized riser reactor at a linear velocity greater than about 1 m/sec, the feed comprising the hydrocarbons, the riser reactor having a plurality of oxygen injection ports located between the bottom and the top of the riser reactor, the plurality of oxygen injection ports dividing the riser reactor into a plurality of segments, wherein the oxidative dehydrogenation catalyst comprises a first component selected from the group consisting of Group VIII metal components and mixtures thereof supported on a support, and wherein the catalyst particles ranges from about 20 μm to about 200 µm. The hydrocarbons and the catalyst are contacted in the riser reactor under dehydrogenation conditions to dehydrogenate the hydrocarbons to form olefins and hydrogen. An oxygen-containing gas is introduced into the plurality of injection ports to oxidize a portion of the hydrogen formed from the dehydrogenation reaction in the segment, an amount of oxygen-containing gas being introduced into each injection port being no more than an amount sufficient to oxidize about 60% of the hydrogen formed in the segment. The olefins are separated from the catalyst, and the olefins are recovered.

DETAILED DESCRIPTION OF THE INVENTION

Figure 1:
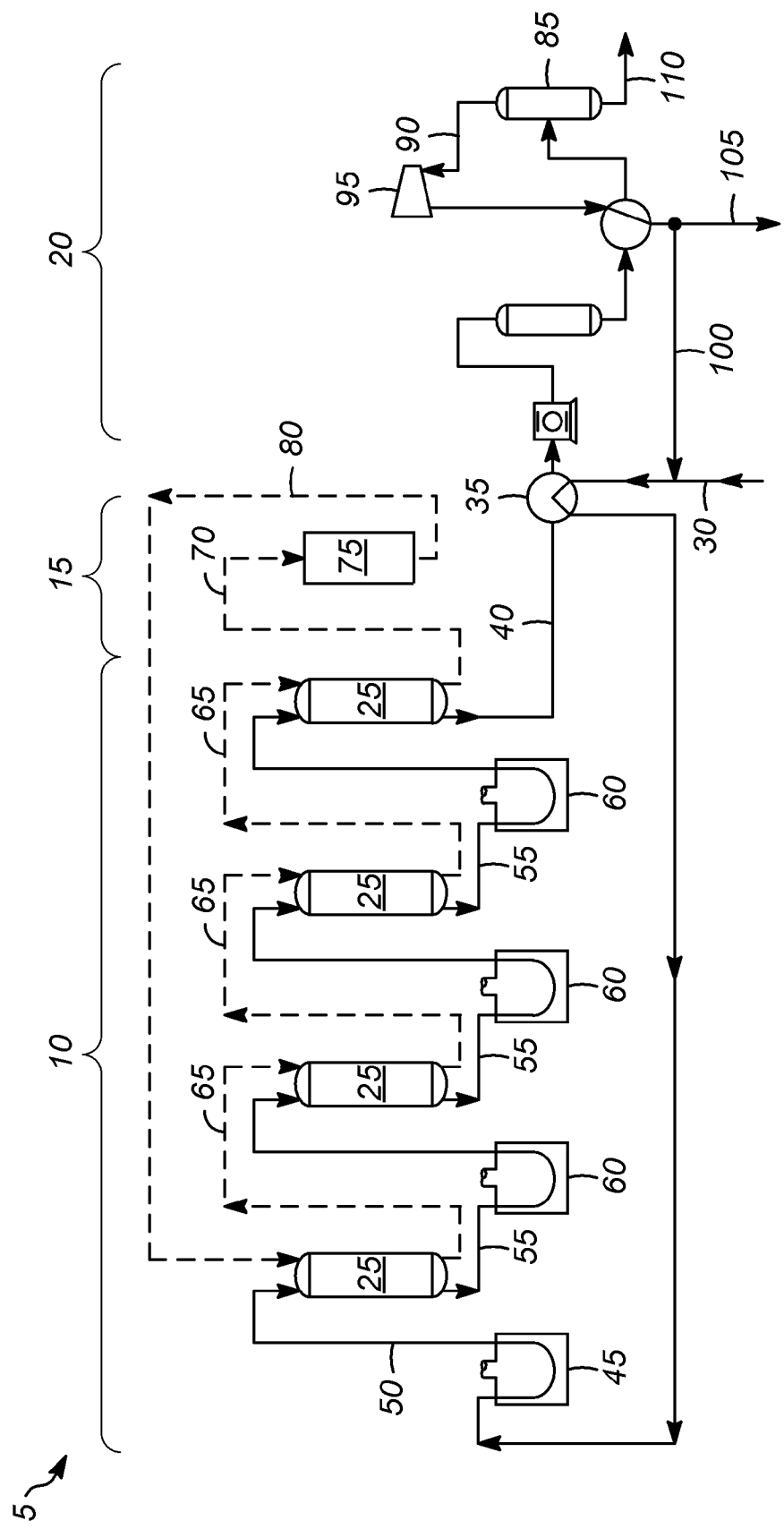
FIG. 1 is an illustration of one embodiment of a prior art moving bed dehydrogenation process.
Figure 2:
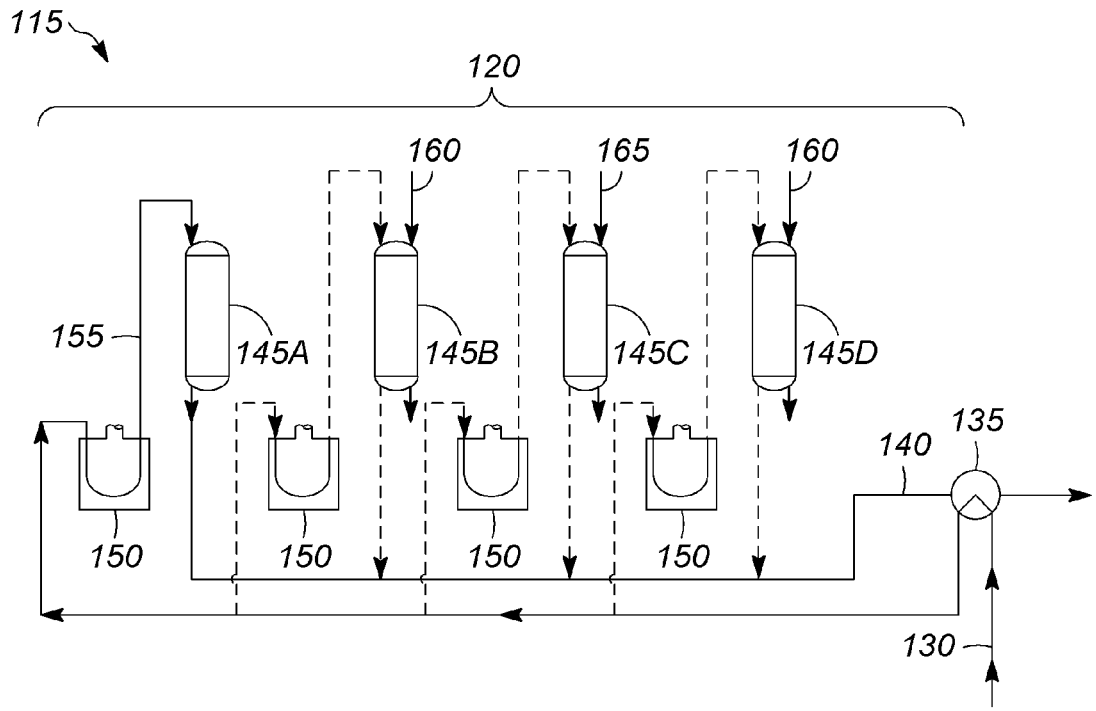
FIG. 2 is an illustration of one embodiment of a prior art cyclic bed dehydrogenation process.

The invention involves performing oxidative dehydrogenation of hydrocarbons in a fluidized riser reactor. Part of the hydrogen produced in the dehydrogenation reaction is oxidized to provide the heat required for the dehydrogenation reaction. The hydrogen consumption and steam production as a diluent shift the equilibrium in the desired direction. Unlike in adiabatic reactors, the hydrocarbon mixture is maintained at the desired reaction temperature. With proper controlled input of oxygen feed at various segments, an increasing temperature profile can be obtained where the maximum temperature is achieved at the reactor outlet, which significantly increases the conversion per pass without a large loss in selectivity.

The oxidative dehydrogenation reaction is performed in a fluidized riser reactor where preheated hydrocarbon feed is fed to the inlet of the riser reactor. Hot catalyst coming from a catalyst surge vessel and catalyst regenerator is mixed and fluidized by the feed vapor at the reactor inlet. The feed and catalyst flow upward in the riser reactor in a co-current flow.

The hydrocarbon feed can include hydrogen, if desired. The hydrogen mixed with the feed can be oxidized in the first preheating zone to bring the temperature to desired T, minimizing thermal cracking.

The hydrocarbon feed can also include optional diluents including, but not limited to, steam, methane, nitrogen, or combinations thereof.

The gaseous hydrocarbon feed and optional diluents are introduced into the riser reactor at a linear velocity greater than about 1 m/sec, or greater than about 2 m/sec, or greater than about 3 m/sec, or about 1 m/sec to about 20 m/sec, or about 2 m/sec to about 10 m/sec.

The dual function catalyst is selective for dehydrogenation of alkanes to olefins and selective for oxidation of hydrogen to steam. It is a single catalyst, and the reactions are performed simultaneously. The hydrogen oxidation is controlled by the oxygen input at each location such that at no point in the riser reactor will the temperature exceed about 650° C. By providing multiple oxygen inlets, the temperature profile can be controlled to be as isothermal as possible in each segment within the range of about 550° C. to about 650° C., or about 600° C. to about 640° C. The temperature ranges mentioned here are for dehydrogenation of propane to propylene or for butanes to butylenes. As mentioned earlier, for $C_2$ to $C_{20}$ paraffins, this temperature range is about 400° C. to about 700° C.

As the feed and catalyst pass upward through the riser reactor, dehydrogenation takes place, consuming heat and producing hydrogen. An oxygen-containing gas is fed into the riser reactor through multiple inlets along the riser pipe to oxidize part of the produced hydrogen and compensate for the consumed heat of reaction. The oxygen inlets divide the riser reactor into segments. There are at least 2 oxygen inlets, or at least 3, or at least 4, or at least 5, or at least 6, or at least 7, or at least 8, or at least 9, or at least 10, or more.

The heat of combustion of hydrogen is about twice the heat of dehydrogenation (about 68 kcal/g mol v. about 31 kcal/g mol $H_2$ removed). The amount of oxygen added at any inlet is limited so that no more than about 60%, or no more than about 50%, or between about 40% and about 60%, of the hydrogen produced in the segment is oxidized. This allows the temperature in the riser reactor to be maintained at near isothermal condition or in an increasing temperature profile, but not excessively. It is undesirable to burn all of the hydrogen produced by the dehydrogenation reaction because the temperature would become too high and/or the hydrocarbons will begin to burn.

The riser effluent is routed from the riser reactor outlet to a separator, such as a cyclone, where a gas/solid separation is done. The solid catalyst collected from the bottom of the separator is sent to a hot surge vessel, while the product gas is sent to from the top of the cyclone to a vapor cooler. Quench water or steam can be injected directly downstream of the separator to suppress the cracking reaction, if desired.

The cooled vapor is sent to a water/hydrocarbon separator where water and catalyst fines are collected in the bottom and hydrogen and hydrocarbon are collected from the top. The pressure at the water/hydrocarbon separator is typically less than about 207 kPa (g) (30 psig). The fines can be separated from the water by filtration, centrifugation, or other methods of solid/liquid separation. The hydrocarbon vapors are compressed and sent for further separation as done in conventional dehydrogenation processes.

The hydrocarbons to be dehydrogenated include, but are not limited to, dehydrogenatable $C_2$ to $C_{30}$ or more hydrocarbons, or $C_2$ to $C_{20}$ hydrocarbons, or $C_2$ to $C_{10}$ hydrocarbons, or $C_2$ to $C_4$ hydrocarbons, including paraffins, alkylaromatics, naphthenes and olefins. One group of hydrocarbons which can be dehydrogenated in the process is the group of $C_2$ to $C_{30}$ or more paraffins, or $C_2$ to $C_{10}$ paraffins, or $C_2$ to $C_4$ paraffins. When the feed is $C_2$ to $C_4$ hydrocarbons, the hydrocarbon products from the water/hydrocarbon separator will be gases. If higher hydrocarbons are used, there may be some liquid.

The catalyst is an oxidative dehydrogenation catalyst. This dual function oxidative dehydrogenation catalyst enables dehydrogenation of the hydrocarbon feed and also promotes selective oxidation of hydrogen with added oxygen forming water. The oxidative dehydrogenation catalyst does not supply oxygen for the reaction, that is, the catalyst is not in its oxide form. Rather, the oxygen for the reaction is added to the riser reactor through the plurality of oxygen inlets.

The oxidative dehydrogenation catalyst generally comprises a first component selected from the group consisting of Group VIII metal components and mixtures thereof on a support. The catalyst particles typically range from about 20 µm to about 200 µm, or about 40 µm to about 150 µm.

The ratio of weight of catalyst to weight of hydrocarbons at the inlet of the riser reactor is in a range of about 1:1 to about 100:1, or about 5:1 to about 50:1, or about 5:1 to about 40:1, or about 5:1 to about 30:1.

The oxygen-containing gas can be any suitable oxygen-containing gas, including, but not limited to, pure oxygen, air, or steam diluted oxygen. Steam and/or hydrogen can optionally be injected into the riser reactor with the hydrocarbon feed. If there is no steam, the oxygen and hydrogen can create an explosive mixture or cause the hydrocarbon to burn. Therefore, the oxygen feed concentration is adjusted so that it is out of the flammability envelope in all parts of the riser reactor, e.g., about 6-7%. The steam can be added with the hydrocarbon feed or to the oxygen-containing gas. The amount of oxygen added to the riser reactor is adjusted to obtain the required temperature at the riser reactor outlet.

Most of the catalyst in the hot surge vessel is circulated back to the inlet of the riser reactor, and a portion is sent to a catalyst regenerator. Regenerated catalyst is mixed with the circulating, partially-used hot catalyst from the hot surge vessel before being introduced into the riser reactor inlet.

For propane dehydrogenation, the temperature of the feed entering the riser reactor should be less than about 600° C. to minimize thermal cracking losses in the preheating sections, preferably it is in the range of about 550° C. to about 600° C. If the feed entering the riser reactor is at a temperature of about 550° C., the first segment of the reactor at the inlet of the hydrocarbon feed premixed with a small quantity of hydrogen may be used to selectively oxidize the hydrogen with oxygen introduced in the first segment, thus raising the temperature of the hydrocarbons to a desired dehydrogenation temperature in the range of 600° C. to about 650° C.

The temperature in the riser reactor should be in the range of about 600° C. to about 650° C., or about 620° C. to about 640° C. The temperature is desirably no higher than about 650° C. so that cracking reactions do not occur.

It is desirable to maintain the temperature in each segment to within ±10° C. of a preselected operating temperature for that segment, or within ±5° C. The preselected temperature is within the ranges described above. The preselected temperatures of the segments can be increased from the inlet of the riser reactor to the outlet, if desired.

Activity is a measure of the catalyst's ability to convert reactants into products at a specific set of reaction conditions, that is, at a specified temperature, pressure, contact time, and concentration of diluent such as hydrogen, if any. For dehydrogenation catalyst activity, the conversion or disappearance of hydrocarbons in percent relative to the amount of hydrocarbons in the feedstock is measured. The conversion is at least about 30%, or at least about 35%, or a least about 40%, or at least about 45%, or at least about 50%, or at least about 55%, or at least about 60%, or in the range of about 30% to about 70%, or in the range of about 30% to about 60%.

Selectivity is a measure of the catalyst's ability to convert reactants into the desired product or products relative to the amount of reactants converted. For catalyst selectivity, the amount of olefins in the product, in mole percent, relative to the total moles of the hydrocarbons converted is measured. The selectivity is at least about 70 mol %, or at least about 75 mol %, or at least about 80 mol %, or at least about 85 mol %, or at least about 90 mol %, or at least about 95 mol %.

Figure 4:
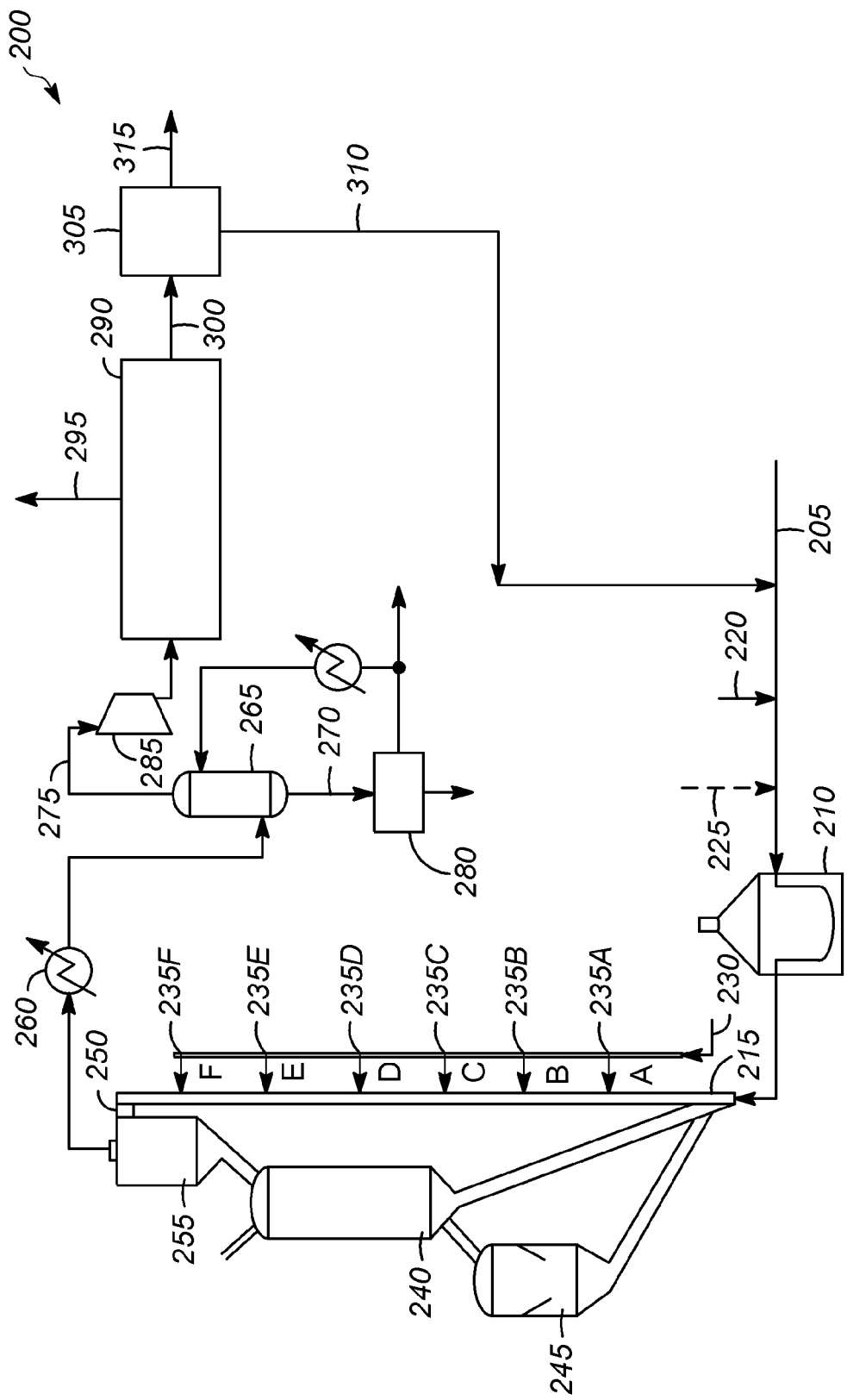
FIG. 4 is an illustration of one embodiment of a fluidized riser reactor oxidized dehydrogenation process.

FIG. 4 illustrates a fluidized riser reactor oxidative dehydrogenation process 200. The hydrocarbon feed 205 is preheated in a preheater 210 before entering riser reactor 215. Steam 220 and optionally hydrogen 225 can be added to the hydrocarbon feed 205. Catalyst from the surge vessel 240 and/or the catalyst regenerator 245 enters the inlet of the riser reactor 215. The hydrocarbon feed 205 in the presence of the catalyst reacts and forms the olefin product and hydrogen.

Oxygen 230 is introduced into the riser reactor 215 at multiple oxygen inlets 235A-F along the riser reactor 215. The oxygen can be any oxygen-containing stream, such as air, pure oxygen, or an oxygen stream containing more oxygen than air. The oxygen inlets 235A-F divide the riser reactor 215 into segments A-F. As discussed above, the amount of oxygen introduced into each oxygen inlet is controlled so that it is no more than the amount sufficient to oxidize 60%, or 50% of the hydrogen formed in the preceding segment.

The temperature of the hydrocarbon feed 205 entering segment A of the riser reactor 215 is typically about 550° C. to about 650° C. The reaction mixture along with the catalyst moves upward through each of the segments, A through F, in the riser reactor 215. The temperature falls as the dehydrogenation of the hydrocarbon feed takes place. However, the endothermic heat of dehydrogenation reaction is carefully compensated via controlled addition of oxygen in each segment. Thus, the temperature at the exit of the riser reactor is typically about 600° C. to 650° C. in order to give the desired conversion of the hydrocarbon feed at the desired selectivity to the product olefinic hydrocarbons.

The effluent 250 from the riser reactor 215 is sent to separator 255, such as a cyclone, where the gas product and unconverted feed are separated from the catalyst.

The catalyst is sent to surge vessel 240. A portion of the catalyst is sent to regenerator 245 where the coke is burned off. Some noble metal catalysts may require reconditioning, such as platinum redistribution. The regenerated catalyst is sent to the inlet of the riser reactor 215. The remainder of the catalyst is sent from the surge vessel 240 to the inlet of the riser reactor 215 where it is combined with the regenerated catalyst and mixed with the hydrocarbon feed 205.

The gas product and unconverted feed is cooled in heater exchanger 260 and sent to a quench tower 265 where the water and fines 270 are separated from the gases 275. The stream 270 is further processed in a separator 280 to separate catalyst fines and dust from the water. A portion of the water can be further cooled and recycled to the quench tower 265 to provide further cooling. The gases 275 are compressed in compressor 285 and separated in a gas liquid separator 290. Gases 295, including hydrogen, nitrogen, and lower alkanes, are separated and recovered or further processed. Liquid olefins and unconverted hydrocarbon feed 300 are separated in column 305. The unreacted hydrocarbon feed 310 can be recycled to the riser reactor 215. The product olefins 315 can be recovered.

In an alternative embodiment, the preheater 210 can be replaced by the heat exchanger 260. In that case, the feed would be heated by the heat from the product gases and unconverted feed coming from the separator 255.

In another alternative, the heat exchanger 260 could be used to make steam 220 for use in the process.

As discussed above, the oxidative dehydrogenation catalyst generally comprises a first component selected from the group consisting of Group VIII metal components and mixtures thereof on a support.

In some embodiments, the oxidative dehydrogenation catalyst includes a second component selected from the group consisting of alkali metal components, alkaline earth metal components, and mixtures thereof.

In some embodiments, the oxidative dehydrogenation catalyst includes a third component selected from the group consisting of tin, germanium, lead, indium, gallium, thallium, and mixtures thereof.

As indicated above, the catalyst includes a first component selected from Group VIII metals or mixtures thereof, with Group VIII noble metals being preferred. The Group VIII noble metal may be selected from the group consisting of platinum, palladium, iridium, rhodium, osmium, ruthenium, or mixtures thereof, with platinum being preferred.

The Group VIII metal component is desirably well dispersed throughout the catalyst. It generally will comprise about 0.01 to 5 wt. %, calculated on an elemental basis, of the final catalytic composite. Preferably, the catalyst comprises about 0.1 to 2.0 wt. % Group VIII metal component, especially about 0.1 to about 2.0 wt. % platinum.

The Group VIII metal component may be incorporated in the catalyst in any suitable manner such as, for example, by coprecipitation or cogelation, ion exchange or impregnation, or deposition from a vapor phase or from an atomic source, or by like procedures either before, while, or after other catalytic components are incorporated. The preferred method of incorporating the Group VIII metal component is to impregnate the support with a solution or suspension of a decomposable compound of a Group VIII metal. For example, platinum may be added to the support by commingling the latter with an aqueous solution of chloroplatinic acid. Another acid, for example, nitric acid or other optional components, may be added to the impregnating solution to further assist in evenly dispersing or fixing the Group VIII metal component in the final catalyst.

The catalyst can also include a second catalytic component comprised of an alkali or alkaline earth component. The alkali or alkaline earth component may be selected from the group consisting of cesium, rubidium, potassium, sodium, and lithium or from the group consisting of barium, strontium, calcium, and magnesium or mixtures of metals from either or both of these groups. It is believed that the alkali and alkaline earth component exists in the final catalyst in an oxidation state above that of the elemental metal. The alkali and alkaline earth component may be present as a compound such as the oxide, for example, or combined with the support or with the other catalytic components.

Preferably the alkali and alkaline earth component is well dispersed throughout the catalytic composite. The alkali or alkaline earth component will preferably comprise 0.9 to 1.1 wt. %, calculated on an elemental basis of the final catalytic composite.

The alkali or alkaline earth component may be incorporated in the catalytic composite in any suitable manner such as, for example, by coprecipitation or cogelation, by ion exchange or impregnation, or by like procedures either before, while, or after other catalytic components are incorporated. A preferred method of incorporating the alkali component is to impregnate the support with a solution of potassium hydroxide.

The catalyst can also include a modifier metal component comprising Group IIIA or IVA metals. The modifier metal component can be selected from the group consisting of tin, germanium, lead, indium, gallium, thallium, and mixtures thereof. The effective amount of the third modifier metal component is preferably uniformly impregnated. Generally, the catalyst will comprise from about 0.01 to about 10 wt. % of the third modifier metal component calculated on an elemental basis on the weight of the final composite. Preferably, the catalyst will comprise from about 0.1 to about 5 wt. % of the third modifier metal component.

The third modifier metal component is preferably tin. Some or all of the tin component may be present in the catalyst in an oxidation state above that of the elemental metal. This component may exist within the composite as a compound such as the oxide, sulfide, halide, oxychloride, aluminate, etc., or in combination with the support or other ingredients of the composite. Preferably, the tin component is used in an amount sufficient to result in the final catalytic composite containing, on an elemental basis, about 0.01 to about 10 wt. % tin, with best results typically obtained with about 0.1 to about 5 wt. % tin.

Suitable tin salts or water-soluble compounds of tin which may be used include stannous bromide, stannous chloride, stannic chloride, stannic chloride pentahydrate, stannic chloride tetrahydrate, stannic chloride trihydrate, stannic chloride diamine, stannic trichloride bromide, stannic chromate, stannous fluoride, stannic fluoride, stannic iodide, stannic sulfate, stannic tartrate, and the like compounds. The utilization of a tin chloride compound, such as stannous or stannic chloride is particularly preferred.

The third component of the catalyst may be composited with the support in any sequence. Thus, the first or second component may be impregnated on the support followed by sequential surface or uniform impregnation of the third component. Alternatively, the third component may be surface or uniformly impregnated on the support followed by impregnation of the other catalytic components.

The catalyst may also contain a halogen component. The halogen component may be fluorine, chlorine, bromine, or iodine, or mixtures thereof. Chlorine is the preferred halogen component. The halogen component is generally present in a combined state with the support and alkali component. Preferably, the halogen component is well dispersed throughout the catalytic composite. The halogen component may comprise from more than 0.01 wt. % to about 15 wt. %, calculated on an elemental basis, of the final catalyst.

The halogen component may be incorporated in the catalyst in any suitable manner, either during the preparation of the carrier material or before, while, or after other catalyst components are incorporated. For example, the alumina sol utilized to form an alumina support may contain halogen and thus contribute at least some portion of the halogen content in the final catalyst composite. Also, the halogen component or a portion thereof may be added to the catalyst composite during the incorporation of the support with other catalyst components, for example, by using chloroplatinic acid to impregnate the platinum component. Also, the halogen component or a portion thereof may be added to the catalyst composite by contacting the catalyst with the halogen or a compound or solution containing the halogen before or after other catalyst components are incorporated with the carrier material. Suitable compounds containing the halogen include acids containing the halogen, for example, hydrochloric acid. Alternatively, the halogen component or a portion thereof may be incorporated by contacting the catalyst with a compound or solution containing the halogen in a subsequent catalyst regeneration step. In the regeneration step, carbon deposited on the catalyst as coke during use of the catalyst in a hydrocarbon conversion process is burned off, and the catalyst and the platinum group component on the catalyst are redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound or solution containing the halogen, such as propylene dichloride, for example, to the hydrocarbon feed stream or to the recycle gas during operation of the hydrocarbon conversion process. The halogen may also be added as chlorine gas ($Cl_2$).

The support can be a porous, absorptive support. It will typically have a surface area of from about 25 to about 500 $m^2/g$. The support should be relatively refractory to the conditions utilized in the hydrocarbon conversion process. Suitable supports are those which have traditionally been utilized in hydrocarbon conversion catalysts such as, for example; (1) activated carbon, coke, or charcoal; (2) silica or silica gel, silicon carbide, clays, and silicates, including synthetically prepared and naturally occurring ones, which may or may not be acid treated, for example, attapulgus clay, china clay, diatomaceous earth, fuller's earth, kaolin, kieselguhr, etc.; (3) ceramics, procelain, crushed firebrick, bauxite; (4) refractory inorganic oxides such as alumina, titanium dioxide, zirconium dioxide, chromium oxide, beryllium oxide, vanadium oxide, cerium oxide, hafnium oxide, zinc oxide, magnesia, boria, thoria, silica-alumina, silica-magnesia, chromia-alumina, alumina-boria, silica-zirconia, etc.; (5) crystalline zeolitic aluminosilicates such as naturally occurring or synthetically prepared mordenite and/or faujasite, for example, either in the hydrogen form or in a form which has been exchanged with metal cations; (6) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (7) combinations of materials from one or more of these groups. In some embodiments, the support is alumina, especially gamma-, eta-, or theta-alumina.

In some embodiments, the support is alumina having a surface area greater than about 50 $m^2/g$, or less than 120 $m^2/g$, or about 50 $m^2/g$ to about 120 $m^2/g$. In addition, in some embodiments, the alumina can have an apparent bulk density (ABD) of about 0.5 $g/cm^3$ or more, or about 0.6 $g/cm^3$ or more. The alumina support may be prepared in any suitable manner from synthetic or naturally occurring raw materials. The support may be formed in any desired shape such as spheres, pills, cakes, extrudates, powders, granules, etc. A preferred shape of alumina is the sphere.

To make alumina spheres, aluminum metal is converted into an alumina sol by reacting it with a suitable peptizing agent and water, and then dropping a mixture of the sol into an oil bath to form spherical particles of the alumina gel. The third modifier metal component may be added to the alumina sol before it is reacted with the peptizing agent and dropped into the hot oil bath. After the alumina particles optionally containing the co-formed third component are shaped, they are dried and calcined. The catalyst particles prepared by this method are sized to ranges from about 20 μm to about 200 μm, and preferably ranges from about 40 μm to about 120 μm with an average size in the range of about 70 μm to 90 μm.

Other shapes of the catalyst carrier material may also be prepared by conventional methods. In one such alternate method slurry of alumina, clay and silica binder with the desired catalyst components is prepared and milled to obtain substantially uniform particle distribution. The milled slurry is then spray dried to produce particles having an average particle size of about 80 μm which are than calcined.

The drying and calcination of the alumina base component helps to impart the catalyst base with the desired characteristics. Calcination temperatures ranging from 600° C. to 950° C. are known to produce alumina comprising essentially crystallites of gamma-alumina. Calcination temperatures of 1100° C. and above are known to promote the formation of alpha-alumina crystallites while temperatures of from 950° C. to 1100° C., and especially from 975° C. to 1050° C. promote the formation of theta-alumina crystallites.

In some embodiments, the support has a surface area of 120 $m^2/g$ or less and a corresponding ABD of 0.50 $g/cm^3$ or more. These characteristics are imparted in the alumina by a final calcination of the alumina at a temperature ranging from 950° C. to 1200° C. In some embodiments, the final calcination step is at conditions sufficient to convert the alumina into theta-alumina. Such conditions would include a calcination temperature closely controlled between 950° C. and 1100° C., and preferably from 975° C. to 1050° C.

The surface area of the catalyst as set forth is derived by the well-known mercury intrusion technique. This method may be used for determining the pore size distribution and pore surface area of porous substances by mercury intrusion using a Micromeritics Auto Pore 9200 Analyzer. In this method, high pressure mercury is forced into the pores of the catalyst particles at incrementally increasing pressures to a maximum of 413,700 kPa (60,000 psia). Pore volume readings are taken at predetermined pressures. A maximum of 85 pressure points can be chosen. Accordingly by this method, a thorough distribution of pore volumes may be determined.

The effect of calcination of an alumina base, especially at the elevated temperatures described here is to densify the alumina base. The densification, i.e. increase in ABD, is caused by a decrease in the overall catalyst pore volume. In addition, the high calcination temperatures cause the existing pores to expand. To accomplish this apparently contradictory mechanism, the catalyst necessarily contracts in size while the existing pores expand. By expanding, the mouths of the existing pores increase so that they become less likely to be plugged or restricted by coke build-up.

In some embodiments, the alumina component is essentially theta-alumina. By "essentially theta-alumina", it is meant that at least 75% of the alumina crystallites are theta-alumina crystallites. The remaining crystallites of alumina will likely be in the form of alpha-alumina or gamma-alumina. However, other forms of alumina crystallites known in the art may also be present. The essentially theta-alumina component can comprise at least 90% crystallites of theta-alumina, if desired.

After the catalyst components have been combined with the support, the resulting catalyst composite will generally be dried at a temperature of from about 100° C. to about 320° C. for a period of typically about 1 to 24 hours or more and thereafter calcined at a temperature of about 320° C. to about 600° C. for a period of about 0.5 to about 10 or more hours. Typically, chlorine-containing compounds are added to air to prevent sintering of catalyst metal components. This final calcination typically does not affect the alumina crystallites or ABD. However, the high temperature calcination of the support may be accomplished at this point if desired. Finally, the calcined catalyst composite is typically subjected to a reduction step before use in the hydrocarbon conversion process. This reduction step is effected at a temperature of about 230° C. to about 650° C. for a period of about 0.5 to about 10 or more hours in a reducing environment, preferably dry hydrogen, the temperature and time being selected to be sufficient to reduce substantially all of the platinum group component to the elemental metallic state.

Suitable catalysts are described in U.S. Pat. Nos. 4,430,517, 4,914,075, and 6,756,340, each of which is incorporated herein by reference.

In one embodiment, the oxidative dehydrogenation catalyst comprises a platinum group component, a Group IVA component, an alkali or alkaline earth component, more than 0.2 weight %, calculated on an elemental basis, of a halogen component and a porous carrier material, wherein the atomic ratio of the alkali or alkaline earth component to the platinum group component is more than 10. The platinum group component is preferably present in the final composite in an amount, calculated on an elemental basis, of about 0.01 to 5 weight %; the Group IVA component is preferably present in an amount of about 0.01 to 5 weight %; the alkali or alkaline earth component is preferably present in an amount of about 0.01 to 15 weight %; and the halogen component is present preferably in an amount of about 0.2 to 15 weight %.

In another embodiment, the oxidative dehydrogenation catalyst comprises a first component selected from Group VIII noble metals, a second component selected from the group consisting of alkali or alkaline earth metals or mixtures thereof, and a third component selected from the group consisting of tin, germanium, lead, indium, gallium, thallium, or mixtures thereof, all on an alumina support having a surface area of 120 m$^2$/g or less and an apparent bulk density of 0.5 g/cm$^3$ or more.

In another embodiment, the oxidative dehydrogenation catalyst comprises a first component selected from Group VIII noble metal components or mixtures thereof, a second component in an amount from 0.9 to 1.1 weight percent, based on the total composite weight selected from the group consisting of alkali or alkaline earth metal components or mixtures thereof and a third component selected from the group consisting of tin, germanium, lead, indium, gallium, thallium and mixtures thereof, all on an alumina support comprising essentially theta-alumina and having a surface area from about 50 to about 120 m$^2$/g and an apparent bulk density of at least 0.5 g/cm$^3$ wherein the mole ratio of the first component to the third component is in the range from about 1.5 to about 1.7.

As mentioned earlier, the amount of oxygen added in each segment needed to maintain the desired conversion and selectivity to the desired product has to be determined. There are numerous ways one can go about it.

Figure 3:
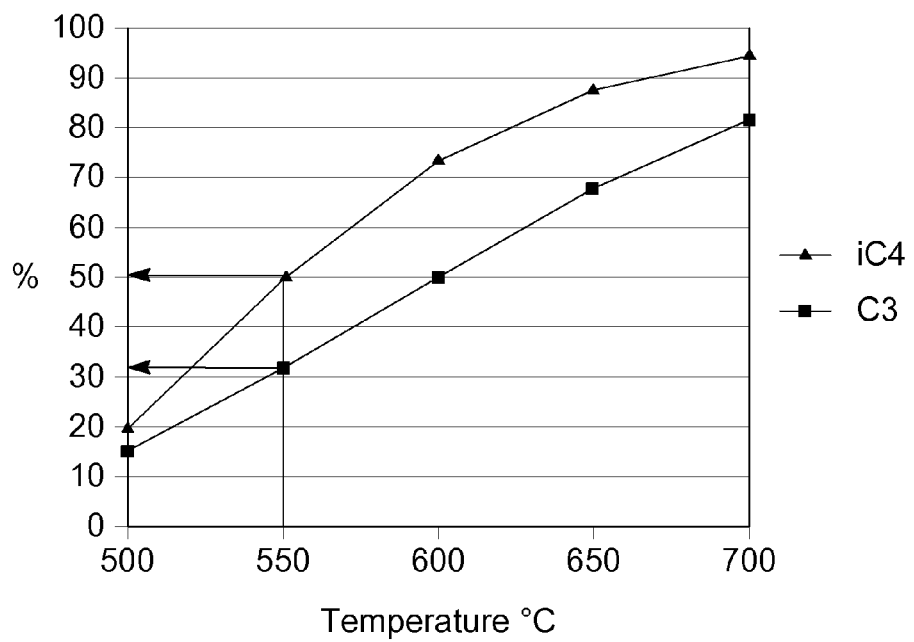
FIG. 3 is a graph showing the propylene and isobutylene equilibrium at 101 kPa (1 atm) with no hydrogen recycle.

FIG. 3 shows the propane and isobutene dehydrogenation equilibrium at 101 kPa (1 atm) pressure. Similar data can be obtained at different pressures and thus for the operating pressure of the dehydrogenation reactor. The heat of combustion of hydrogen is about twice the heat of propane dehydrogenation (about 68 kcal/g mol v. about 31 kcal/g mol H$_2$ removed). Under an ideal condition, with no cracking by-products loss, each mole of propane dehydrogenated produces one mole of propene and one mole of hydrogen. Therefore, to compensate for the endothermic heat of dehydrogenation, the amount of hydrogen that needs to be consumed is less than 50% of the hydrogen produced (31/68 or 46%). This enables one to preselect the temperature required at the outlet of each segment for a desired conversion, and thus the desired output composition at the outlet of each segment. Therefore, the oxygen input can be controlled by measuring the temperature at the outlet of each segment.

In another mode, sampling points may be provided in the outlet of each segment to determine the composition of the reactant mixture at the outlet of each segment and use it to control the oxygen input.

If desired, an emergency shutoff of oxygen input can be provided at some temperature higher (e.g., 10° C., or 20° C.) than the desired temperature to avoid any excess combustion of hydrogen as well as the feed hydrocarbon.

EXAMPLE

A riser reactor with nine (9) injection ports was run under the following conditions. The riser was 1.83 m (6 ft) in diameter, and 21.2 m (69.4 ft) in height and had an overall volume of 55.6 m$^3$ (1965 ft$^3$). The riser inlet velocity was 9.2 m/s (31.2 ft/s), and the outlet velocity was 17.9 m/s (58.7 ft/s). The propylene production was 28,125 kg/hr. The catalyst to propane ratio was 30 wt/wt. The riser inlet temperature was 610° C. The riser inlet pressure was 83 kPa (g) (12 psig), and the riser outlet pressure was 55 kPa (g) (8.0 psig). Steam was added at the riser inlet at 1.0 mol/mol Steam/Propane ratio, and no hydrogen was added. Air was injected along the riser reactor at the 9 injection ports. The air injection rates and distances between the injection points were selected to achieve near isothermal conditions. The results are shown below.

TABLE 1

| Riser Section | Riser Vol, % | Tin, C. | Tout, C. | Pin, psig | Air Inj, kmol/hr |
|---|---|---|---|---|---|
| 1 | 3.0 | 609.0 | 601.5 | 12.0 | 0.0 |
| 2 | 3.8 | 610.0 | 605.0 | 11.9 | 301.4 |
| 3 | 4.7 | 610.0 | 605.3 | 11.7 | 178.2 |
| 4 | 5.9 | 610.0 | 605.3 | 11.5 | 168.0 |
| 5 | 7.3 | 610.0 | 605.2 | 11.3 | 168.5 |
| 6 | 9.2 | 610.0 | 605.2 | 11.0 | 171.1 |
| 7 | 11.5 | 610.0 | 605.2 | 10.6 | 171.7 |
| 8 | 14.3 | 610.0 | 605.4 | 10.2 | 171.1 |
| 9 | 17.9 | 610.0 | 605.7 | 9.6 | 164.4 |
| 10 | 22.4 | 610.0 | 606.3 | 8.9 | 152.7 |

The propane conversion was 65.1% compared with 33.9% for an adiabatic reactor. The propylene selectivity was 90.1 wt % compared to 84.7% for the adiabatic reactor.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for oxidative dehydrogenation of paraffins comprising:
   introducing a feed comprising the paraffins and a dual functional oxidative dehydrogenation catalyst into an inlet at a bottom of a fluidized riser reactor at a linear velocity greater than about 1 m/sec, the riser reactor having a plurality of oxygen injection ports located between the bottom and the top of the riser reactor, the plurality of oxygen injection ports dividing the riser reactor into a plurality of segments,
   contacting the paraffins and the catalyst in the riser reactor under dehydrogenation conditions to dehydrogenate the paraffins to form corresponding olefins and hydrogen;

introducing an oxygen-containing gas into the plurality of injection ports to oxidize 60 mole % or less of the hydrogen formed from the dehydrogenation reaction in the segment and controlling the oxygen introduction to each section to maintain a near isothermal or increasing temperature profile along the reactor;

separating the olefins from the catalyst; and recovering the olefins;

wherein the catalyst comprises at least one Group VIII noble metal component in an amount ranging from about 0.01 to about 5 wt %, calculated on an elemental basis of the catalyst, the catalyst is supported on a support, and the catalyst particles size are in the range from about 20 nm to about 200 nm.

2. The process of claim 1 wherein the feed further comprises a diluent.

3. The process of claim 2 wherein the diluent comprises steam, methane, nitrogen, or combinations thereof.

4. The process of claim 1 further comprising regenerating at least a portion of the catalyst and returning the regenerated catalyst to the riser inlet.

5. The process of claim 1 wherein the linear velocity of the feed is in the range of about 2 to about 10 m/sec.

6. The process of claim 1 wherein a temperature in each segment varies less than about ±10° C. from a preselected operating temperature.

7. The process of claim 1 wherein the paraffins are $C_2$ to $C_{20}$ paraffins.

8. The process of claim 1 wherein the feed is preheated.

9. The process of claim 1 further comprising separating unreacted paraffins from the olefins, and recycling at least a portion of the unreacted paraffins to the fluidized riser reactor.

10. The process of claim 1 wherein a temperature in the fluidized riser reactor is less than about 650° C.

11. The process of claim 1 wherein a temperature of the feed at the inlet of the riser reactor is in a range of about 550° C. to about 600° C.

12. The process of claim 1 further comprising introducing steam with the oxygen-containing gas.

13. The process of claim 1 further comprising cooling the olefins after separating the olefins from the catalyst.

14. The process of claim 1 wherein a ratio of weight of catalyst to weight of paraffins at the inlet of the riser reactor is in a range of about 5:1 to about 50:1.

15. The process of claim 1 wherein the conversion of paraffins is at least about 30%.

16. The process of claim 1 wherein the paraffins are dehydrogenated to the corresponding olefins with a selectivity of at least about 70 mol %.

17. The process of claim 1 wherein the support comprises essentially alumina, said support having a surface area of greater than about 50 $m^2/g$ and an apparent bulk density of at least 0.5 $g/cm^3$.

18. The process of claim 1 wherein the catalyst further comprises an alkali metal, an alkaline earth metal, or mixtures thereof.

19. The process of claim 1 wherein the catalyst further comprises tin, germanium, lead, indium, gallium, thallium, or mixtures thereof.

20. The process of claim 1 wherein introducing the oxygen-containing gas into each injection port oxidizes between about 40 and about 60 mol % of the hydrogen formed in the segment.

* * * * *